(12) United States Patent
Namgoong et al.

(10) Patent No.: US 6,538,032 B1
(45) Date of Patent: Mar. 25, 2003

(54) PHYTOSPHINGOSINE DERIVATIVES WITH ANTITUMOR ACTIVITY

(75) Inventors: Sung Keon Namgoong, Seoul (KR); Seon Yi Park, Seoul (KR)

(73) Assignee: Charmzone Co., Ltd., Seoul (KR)

( * ) Notice: Subject to any disclaimer, the term of this patent is extended or adjusted under 35 U.S.C. 154(b) by 0 days.

(21) Appl. No.: 09/947,404

(22) Filed: Sep. 7, 2001

(51) Int. Cl.[7] .............................................. A61K 31/14
(52) U.S. Cl. ...................... 514/642; 564/503; 564/293; 564/292; 564/291
(58) Field of Search ................................ 564/503, 291, 564/293, 292; 514/642

(56) References Cited

U.S. PATENT DOCUMENTS 6,031,135 A * 2/2000 Ruan et al. ................. 564/292

FOREIGN PATENT DOCUMENTS

| FR | 2794366 | * 12/2000 |
|---|---|---|
| KR | 1999-0078610 | 11/1999 |

OTHER PUBLICATIONS

Dahiya et al, Cancer Research, vol. 47, p 1031–1035, 1987.*
Alberts, D. S. et al., "Safety Aspects of Pegylated Liposomal Doxorubicin in Patients with Cancer", Drugs 1997, 54 Suppl. 4, pp. 30–35, (1997).
Grunaug, M. et al., "Liposomal Doxorubicin in Pulmonary Kapsi's Sarcoma: Improved Survival as Compared to Patients without Liposomal Doxorubicin", Eur J Med Res., vol. 3, pp. 13–19, (1998).
Park, S. Y., "Synthesis of Phytosphingosine Derivatives for Efficient Cationic Liposome–Based DNA–Transfection System" (Part I) and "A Study for Conversion from Penicillin G to L–Penicillamine" (Part II), Masters Thesis, Seoul Women's University, Graduate School, Dept. of Chemistry, 2001.
Paukku, T. et al., "Novel Cationic Liposomes for DNA–Transfection with High Efficiency and Low Toxicity", CPL, 87 pp. 23–29, (1997).
Park, Y. S. et al., "Liposomal N,N,N–Trimethylsphingosine (TMS) as an Inhibitor of B16 Melanoma Cell Growth and Metastasis with Reduced Toxicity and Enhanced Drug Efficacy Compared to Free TMS: Cell Membrane Signaling as a Target in Cancer Therapy III[1]", Cancer Research 54, pp. 2213–2217, (1994).

Hannun, Y. A., "Functions of Ceramide in Coordinating Cellular Responses to Stress", Science vol. 274, pp. 1855–1859, (1996).
Bibel, D. J. et al., "Antimicrobial Activity of Sphingosines", Journal of Investigative Dermatology, vol. 98, No. pp. 273, (1992).
Bibel, D. J. et al., "Topical Shingolipids in Antisepsis and Antifungal Therapy", Clinical and Experimental Dermatology, 20, pp. 395–400, (1995).
Weiner, N. et al., "Liposomes: A Novel Topical Delivery System for Pharmaceutical and Cosmetic Applications", Journal of Drug Targeting, vol. 2, pp. 405–410, (1994).
Heinemann, V. et al., "Pharmacokinetics of Liposomal Amphotericin B (AmBisome) in Critically Ill Patients", Antimicrobial Agents and Chemotherapy, pp. 1275–1280, (1997).
Braun, F. et al., "Is Liposomal Amphotericin B (Ambisome) an Effective Prophylaxis of Mycotic Infections after Liver Transplantation?", Transplantation Proceedings, 30, pp. 1481–1483 (1998).

* cited by examiner

Primary Examiner—Shailendra Kumar
(74) Attorney, Agent, or Firm—Finnegan, Henderson, Farabow, Garrett & Dunner, LLP

(57) ABSTRACT

The present invention relates to an antitumor agent containing a phytosphingosine derivative, and more specifically, to an antitumor agent containing a phytosphingosine derivative of formula I as an active ingredient,

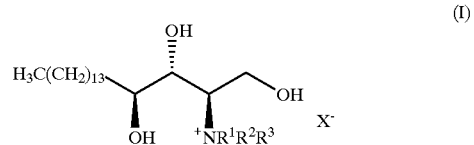

(I)

wherein $R^1$, $R^2$ and $R^3$ respectively represents a hydrogen atom or a $C_1$–$C_8$ alkyl group; and X represents an atom or an atomic group containing a halogen atom, a hydroxyl group, an alkyl sulfonate group or an aryl sulfonate group.

10 Claims, 4 Drawing Sheets

PHYTOSPHINGOSINE DERIVATIVES WITH ANTITUMOR ACTIVITY

FIELD OF THE INVENTION

The present invention relates to an antitumor agent containing a phytosphingosine derivative, and more specifically, to an antitumor agent containing a phytosphingosine derivative of formula I as an active ingredient,

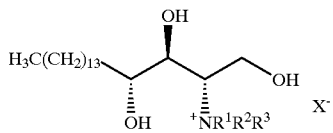

(I)

wherein $R^1$, $R^2$ and $R^3$ respectively represents a hydrogen atom or a $C_1$–$C_8$ alkyl group; and X represents an atom or an atomic group containing a halogen atom, a hydroxyl group, an alkyl sulfonate group or an aryl sulfonate group.

BACKGROUND OF THE INVENTION

Lipids that form a cell membrane generally consist of phospholipid, glycolipid and sphingolipid. These lipids are amphipathic substances and they spontaneously generate completely closed vesicles similar to a cell membrane called 'liposomes' upon dispersion in water.

Liposomes can be prepared by using one kind or combining a few of lipids mentioned in the above. Liposomes are known as a good carrier in a drug delivery system. When pharmaceutical agents are incorporated in the liposomes, the hydrophilic portion of a drug is encapsulated into the internal aqueous phase of the liposomes while the hydrophobic portion of a drug is inserted in bilayer of liposomes. As a drug carrier, liposomes can perform accurate delivery of a desired drug in the diseased part and even small amount of drug can be delivered by liposomes. Therefore, liposomes can seriously reduce side effects such as multi-drug resistance in a heavy dosage of drugs. The applications of liposomes as a drug carrier have been expanded recently to cover a variety of fields such as antigens, genes, pharmaceutical drugs including Doxorubicin (an antitumor agent), Amphotericin B (an antifungal agent), other chemical drugs and also a cosmetic field (M. Grunaug et al., *Eur. J. Med. Res.* 21, 13–19, 1998; D. S. Alberts abd D. J. Garcia, *Drugs*, 54, 30–35, 1997; F. Braun, et al., *Transplant Proc.* 30, 1481–1483, 1998; V. Heinemann et al., *Antimicrob. Agents Chemother.* 41, 1275–1280, 1997; N. Weiner et al., *J. Drug Target*, 2, 405–410, 1994).

Sphingoid bases are present in humans as phytosphingosin (PhytoS), sphingosine (SPN) and sphinganine, which are amino alcohols having 18 carbon atoms, respectively. These compounds have several stereocenters and D-erythro arrangement at position 3 is discovered in nature. SPN and sphinganine are found in all the tissues of human body while PhytoS is present only in horny layer of human skin. Extensive studies on SPN and its derivatives were initiated at early 1990s and the studies were expedited as these were found to be powerful inhibitors of PKC (protein kinase C). Moreover, the SPN and its derivatives were found to be involved in numerous cellular activities even at low concentration (D. J. Bibel et al., *Clin. Exper. Dermatol.*, 20, 395–400, 1995; D. J. Bibel, *J. Invest. Dermatol.*, 98, 269–273, 1992; Y. A. Hannun, *Science*, 274, 1855–1859, 1996). These activities being exhibited mostly in horny layer, the interest on the PhytoS has been much increased, however, they are very expensive and also not much had been known about the methods to synthesize their derivatives and their biological activities. In particular, N,N-dimethyl sphingosine (DMS) and N,N,N-trimethyl sphingosinium halide (hereinafter referred to as TMS.hal), derivatives of SPN, are known to be superior to SPN with respect to their inhibitory activities against PKC and are also known to inhibit the growth of various cancer cells both in vivo and in vitro. In addition, it was also revealed that TMS.hal has an antitumor activity and an anti-metastatic activity in murine B16/BL6 melanoma cell line which utilizes liposomal TMS, wherein the mole ratio of egg phosphatidylcholine (egg PC): cholesterol (Chol): TMS.hal is 4.5:4.5:1. However, there is required a relatively large amount of TMS.hal (e.g., about 0.1–0.3 mg/mouse) to exhibit the above-mentioned effects and this often results in side effects such as hemolysis, hemoglobinuria and an inflammatory response. The efforts to resolve these toxicities were carried out by using liposome technology and the results indicated that liposomal TMS.hal was shown non-toxic and was also more effective in in vivo system in inhibiting the growth of cancer cells as well as metastasis as compared to the TMS.hal without liposomes utilization (Y. S. Park, S. Hakomori, S. Kawa, F. Ruan, and Y. Igarashi, *Cancer Res.*, 54, 2213–2217, 1994).

There has been a report on phytoS, whose structure is very similar to that of SPN, that reveals the difference in efficiency of DNA transfection in in vitro systems of KK-1, COS-7 and MSC-1 cells due to the difference in the formulation of a helper lipid (T. Paukku et al., *Chem. Phys. Lipids*, 87, 23–29, 1997). The phytoS is also known to have an excellent anti-microbial activity for a wide range of microbes and can alleviate skin irritations by secreting interleukin as a PKC inhibitor. N,N,N-trimethyl phytosphingosinium halide (TMP.hal), a derivative of phytoS, was recently published (Korean Unexamined Patent No. 1999-78610), wherein the derivative is described as a cosmetic component with its use limited to skin protection. Nevertheless, there has been no prior example showing that TMP.hal is an antitumor agent.

SUMMARY OF THE INVENTION

The inventors of the present invention manufactured liposomes that contain a derivative of phytosphingosine of the above formula I in various compositions and confirmed their antitumor activity as well as the anti-metastatic activity. Therefore, the object of the present invention is to provide a phytosphingosine derivative of formula I having an antitumor activity and also to provide antitumor agents comprising the phytosphingosine derivative.

DETAILED DESCRIPTION OF THE PREFERRED EMBODIMENTS

Figure 1:
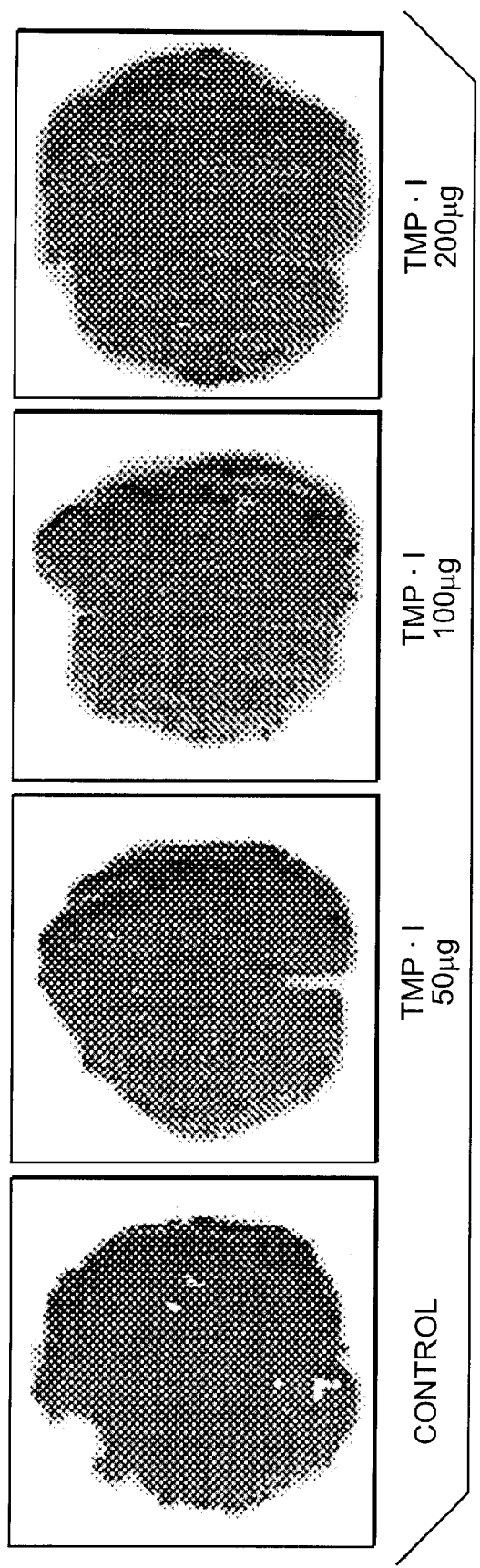
FIG. 1 shows pictures representing the anti-metastatic activity of N,N,N-trimethylsphingosinium iodide (hereinafter referred to as TMP.I) liposomes on a melanoma cell according to TMP.I content.

The present invention relates to an antitumor agent containing a phytosphingosine derivative of the following formula I as an active ingredient.

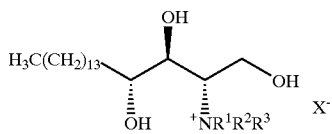

(I)

In the above formula I, $R^1$, $R^2$ and $R^3$ respectively represents a hydrogen atom or a $C_1$–$C_8$ alkyl group; and X represents an atom or an atomic group containing a halogen atom, a hydroxyl group, an alkyl sulfonate group or an aryl sulfonate group.

The antitumor agent of the present invention contains the above phytosphingosine derivative in the form of a liposome or an emulsion, and it can also contain other ingredients such as an anti-angiogenic agent or doxorubicin, an antitumor agent having cytotoxic activity in addition to the phytosphingosine derivative.

The present invention is described in greater detail as set forth hereunder.

The present invention relates to an antitumor agent comprising a phytosphingosine derivative (hereinafter referred to as TMP) of the above formula I which is manufactured in the form of a liposome or an emulsion. As a TMP of the present invention, it is preferred to use N,N,N-trimethylphytosphingosinium halide (TMP.hal), and more preferably N,N,N-trimethylphytosphingosinium iodide (TMP.I).

A variety of compositions of anti-metastatic liposomes were prepared in the present invention. The results showed that DPPC/Chol/TMP or DPPC/Chol/PEG-PE/TMP compositions of liposomes had excellent anti-metastatic activity and also there was a synergistic effect in the anti-metastatic activity when they were used in combination with an anti-angiogenic agent. DPPC/Chol/TMP compositions of liposomes were not only able to inhibit metastasis to lung but they also inhibited the growth of LLC cancer cells.

In the present invention, where a cytotoxicity cancer drug is used along with anti-metastatic liposomes, the anti-metastatic effect became enhanced. The case is when doxorubicin was used with TMP liposomes as compared to when doxorubicin was used alone.

In the present invention, cytotoxic effect of TMP liposomes was examined by using a human hepatomna cell line and a mouse melanoma cell line. The results showed that the TMP liposomes had cytotoxicity in a human hepatoma cell but not in a mouse melanoma cell. A test for acute toxicity was performed in mice and there was no toxic effect observed.

The antitumor agent of the present invention contains a phytosphingosine derivative of the formula I as an active ingredient, and a final preparation can be provided in a form of powder, granule, capsule and injection by mixing it with a pharmaceutically acceptable carrier, an excipient and a diluent. Medications can be administered both in oral and parenteral administrations, and the bioavailability will be more effective if administered after the agent is prepared as an emulsion or a liposome type.

The dosage of the antitumor agent of the present invention can vary depending on the rate of body absorption, body weight, age, sex, health condition, diet, interval of administration, method of administration, excretion rate, seriousness of illness and the like. The preferred amount of dosage is about 0.5–1 mg/kg of body weight. The antitumor agent should be prepared considering the effective range of the dosage and thus manufactured unit preparations can be administered several times at regular intervals or according to a specialized method of dosage upon the decision of a specialist who is in charge of the supervision and observation of the medication along with a subject's request.

Although this invention is described in its preferred form with a certain degree of particularity, it is appreciated by those skilled in the art that the present disclosure of the preferred form has been made only by way of following examples and that numerous changes in the details of the construction, combination, and arrangement of parts may be resorted to without departing from the spirit and scope of the invention.

EXAMPLE 1

Synthesis of N,N,N-trimethylphytosphingosinium iodide (TMP.I)

To 3 mL of methanol, 0.30 g of phytosphingosine (0.946 mmol), 0.523 g of $K_2CO_3$ (3.79 mmol) and 0.298 mL of iodomethane (4.73 mmol) were aded, and the reaction mixture was stirred for 4 hr at 50° C. The solvent was evaporated under reduced pressure and 4 mL of distilled water was added to the resulting mixture. The solution was extracted with 8 mL of ethyl acetate, dried ($Na_2SO_4$), filtered. The ethyl acetate was evaporated to give 0.26 g, of white solid product.

Yield: 76% mp: 210–213° C.

IR(KBr) υ max: 3009 (OH), 2918, 2850 (C—H) $cm^{-1}$ $^1$H NMR (600 MHz, DMSO-$d_6$): δ3.95 (dd, 1H, CH2O, J=14.4 Hz), 3.89 (dd, $^1$H $CH_2O$, J=14.4 Hz), 3.76 (d, 1H, J=8.7 Hz), 3.6 (dd, 1H), 3.11 (s, 9H, $N^+CH_3$), 1.68 (m, 1H, $CH_2$), 1.48 (m, 1H, $CH_2$), 1.23 (s, 24H, $CH_2$), 0.84 (t, 3H, $CH_3$) ppm $^{13}$C NMR (600 GHz, DMSO-$d_6$): δ76.80, 71.01, 55.69, 52.18, 33.21, 31.21, 30.60, 29.15, 29.03, 28.99, 28.93, 28.62, 24.87, 22.00, 13.84 ppm MS (FAB, Glycerol, m/z): 361 ($M^+$).

EXAMPLE 2

Synthesis of N,N,N-trimethylphytosphingosinium p-toluenesulfonate

To 5 mL of methanol, 0.50 g of phytosphingosine (1.575 mmol), 1.61.2 g of $K_2CO_3$ (9.449 mmol) and 1.188 mL of methyl p-toluenesulfonate (7.874 mmol) were aded, and the reaction mixture was stirred for 3 hr at 50° C. The solvent was evaporated under reduced pressure and 5 mL of distilled water was added to the resulting mixture. The solution was extracted with 10 mL of ethyl acetate, dried ($Na_2SO_4$), filtered. The ethyl acetate was evaporated to give 0.46 g of white solid product.

Yield: 55% mp: 185–186° C.

IR (KBr) υ max: 3326 (OH), 2920, 2852 (C—H) $cm^{-1}$ $^1$H NMR (500 MHz, $CD_3OD$): δ7.70 (d, 2H, arom H, J=8.2 Hz), 7.23 (d, 2H, arom H, J=8.0 Hz), 4.1.6 (dd, 1H, $CH_2O$, J=14.4 Hz), 4.09 (dd, 1H, $CH_2O$, J=1.4.4 Hz), 3.89

(d, 1H, J=8.7 Hz), 3.73 (dd, 1H), 3.44 (t, 1H), 3.21 (s, 9H, $N^+CH_3$), 2.37 (s, 3H, Ph—$CH_3$), 1.81 (m, 1H, $CH_2$), 1.58 (m, 1H, $CH_2$), 1.29 (s, 24H, $CH_2$), 0.90 (t, 3H, $CH_3$) ppm $^{13}C$ NMR (500 MHz, $CD_3OD$): δ142.07, 140.16, 128.31, 125.45, 76.73, 71.56, 56.09, 52.21, 33.25, 31.56, 29.28, 29.26, 28.96, 25.03, 22.22, 19.81, 12.93 ppm.

EXAMPLE 3

Preparation of Liposomes (1) Preparation of MLV (Multilamellar Vesicles) and SUV (Small Unilamellar Vesicles)

Phospholipid was added into a glass vial and dissolved in an organic solvent ($CHCl_3$). A thin lipid film was formed within the glass vial while removing the organic solvent completely by using a nitrogen gas or a rotary evaporator. Then, phosphate-buffered saline (PBS) was added and gently shaken at room temperature for sufficient hydration, and then the mixture was vortexed vigorously to disperse the thin lipid film of the phospholipid and finally formed multilamellar vesicles (MLV).

Thus obtained MLV was converted into small unilamellar vesicles (SUV) by using a sonicator. In addition, liposomes of desired size were also prepared by passing the SUV through a proper polycarbonate membrane filter under a high pressure by using an extruder and were used for the experiment subsequently.

(2) Preparation of Anti-metastasis Liposomes

Liposomes comprising various phospholipids and TMP, an anti-metastasis compound, were prepared as follows.

TMP and DOPE, a neutral lipid, were mixed in 1:1 (w/w) ratio, dissolved in an organic solvent in a 20 mL glass vial, and then evaporated under reduced pressure in the presence of a nitrogen gas. Upon formation of a thin lipid film, the film was completely dried, hydrated with distilled water or 5% dextrose, and then cationic liposomes were finally prepared by means of vortex or sonication. TMP was added to a composition comprising egg-derived 70% phosphotidylcholine (PC); a mixture of 1:1 mole ratio of 100% egg PC and cholesterol (Chol); a mixture of 1:1 mole ratio of dipalmitoyl phosphatidylcholine (DPPC) and Chol; a mixture of 5:5:1 mole ratio of DPPC, Chol and phosphotidylethanolamine-polyethylene glycol (PE-PEG), dissolved in an organic solvent, and formed a thin lipid film within the glass vial while completely removing the organic solvent by using a rotary evaporator. Then, the film was hydrated sufficiently at room temperature by adding PBS followed by the dispersion of the thin membrane of the phospholipid, and then the anti-metastatic liposomes were obtained by vortex or sonication.

EXAMPLE 4

Preparation of an Emulsion with an Anti-metastatic Activity and the Measurement of Physical Properties (1) Preparation of an Emulsion 70% egg PC and TMP were dispersed in olive oil, added with glycerol and a dab of tween 20, added with distilled water and sonicated to generate an emulsion. Thus obtained emulsion was passed through a 0.2 μm membrane filter to be used.

(2) Stability Test of Liposomes and Emulsions

Various compositions of liposomes and emulsions comprising TMP were prepared and stored at 4° C. The change in size of liposomes was measured by using zetasizer and the stability of liposomes and emulsions according to the compositions of phospholipids were measured.

EXAMPLE 5

Analysis of in vivo Anti-metastasis

Direct lung metastasis in in vivo system was observed in a C57/BL6 mouse using B16F10 melanoma cells. Various concentrations of melanoma cells were injected, through the tail vein of a mouse of (PBS, $2\times10^4$, $2\times10^5$ and $2\times10^6$) to determine the proper concentration of melanoma cells for administration. After 15 days of the injection, lungs were removed after anesthesia and the cancerous colonies present in the lungs were examined.

Further, proper concentration of melanoma cells determined in the above experiment was injected through the tail vein of the C57/BL6 mice to examine the anti-metastatic effect of the aforementioned TMP-containing anti-metastatic liposomes and emulsions. After 60–90 min of the tumor cell injection, 250 μg of TMP in the liposomes prepared was administered to each mouse and the second and the third administrations were performed 3 days and 6 days after the injection of the melanoma cells, respectively. When needed, the fourth administration was performed 9 days after the injection. Lungs were removed on day 15 and its cancerous colonies were examined.

EXAMPLE 6

Measurement of Cytotoxicity and in vivo Toxicity of TMP Liposomes

Cytotoxic effects of TMP liposomes on cancer cells were examined by using human hepatoma cell line SNU398 and murine melanoma cell line B16F10. The SNU398 and B16F10 were trypsinized and then washed with serum-free medium (RPMI-1640). They were then dyed with trypan blue for cell count, plated on a 48-well plate with $1\times10^5$ cells/mL, and then treated with various concentrations of cationic liposomes comprising TMP. After 3 days, they were dyed again with trypan blue and the reduction of viable cells was examined.

For the examination of in vivo toxicity of TMP liposomes, they were injected via intravenous injection or intraperitoneal injection and the lethality of mice were measured.

EXAMPLE 7

Analysis of the Inhibition of in vivo Growth of Cancer Cells

The inhibition of cancer cell growth in vivo system was examined in BDF1 mice using Lewis lung carcinoma (LLC) cells. The concentration of LLC cells used was such that each mouse was injected with one million carcinoma cells via subcutaneous injection to induce a cancer. One hundred microliter of TMP liposome (TMP 100 μg) was injected intraperitoneally and intravenously, respectively, 1 day, 3 days, 6 days and 9 days after the injection of the above LLC cells. As a positive control, AG3340 (Agouron Pharmaceuticals Co., Ltd., USA), known as an MMP-2 (matrix metaloproteinasse-2) inhibitor, was suspended in 0.2% tween/0.5% carboxymethyl cellulose and 2 mg of the resulting suspension was intraperitoneally injected daily. Twenty one days after the injection of the LLC cells, each mouse was killed by dislocating cervical vertebra and then the change of cancer volume was examined and photographed.

EXAMPLE 8

Preparation of Tablets

| Active Ingredient | 1 g |
|---|---|
| Lactose | 7 g |
| Crystalline Cellulose | 1.5 g |
| Magnesium Stearate | 0.5 g |
| Total | 10 g |

The above components were mixed together after crushing them into small pieces and tablets were prepared by direct tableting method. The total amount of each tablet was 500 mg and the active ingredient accounted for 50 mg.

EXAMPLE 9

Preparation of Powder Type

| Active Ingredient | 1 g |
|---|---|
| Corn Starch | 5 g |
| Carboxy Cellulose | 4 g |
| Total | 10 g |

The above components were mixed together after crushing them into small pieces and prepared powder type. Five hundred milligram of powder was added into a soft capsule and a capsule type preparation was manufactured.

Experimental Example 1

First, the anti-metastatic activity of TMP.I in in vivo system was examined. The metastasis of cancer was examined in four different groups of mice having different B16F10 melanoma cell concentrations of $2\times10^4$, $2\times10^5$, $2\times10^6$ and PBS to determine the number of cancer cells suitable for the observation of the metastasis. The lungs of the mice were removed after 15 days of tail vein injection and examined. The result revealed that the size of lung obtained from the group injected with $2\times10^6$ B16F10 melanoma cell concentration grew larger and finally a large number of colonies were formed. In contrast, the lungs obtained from the groups treated with $2\times10^4$ and PBS did not show any noticeable changes in its size and also did not display the production of tumor colony while the one obtained from the group treated with $2\times10^5$ showed the presence of a small number of colonies and the number of colonies continuously increased until after 21 days of the treatment. Therefore, the appropriate concentration of melanoma cell for the experiment of TMP.I anti-metastasis was determined as $2\times10^5$.

The experimental mice of each group were administered with 300 µg of TMP.I derivatives, respectively, one day, 3 days and 6 days after the injection of B16F10. The lung obtained 15 days after the injection was smaller than that in a control group and colony numbers were also remarkably decreased (Table 1).

TABLE 1

Result of Anti-metastatic Activity of DOPE/TMP Liposomes

| Classification | Dose of TMP-I (µg) | No. of Colonies |
|---|---|---|
| PBS | — | 200 ± 20 |
| DOPE/TMP-I Liposome (1:1 wt ratio) | 300 | 30 ± 15 |

Experimental Example 2

The anti-metastatic activities of TMP.I were examined according to different liposomes compositions. Liposomes were prepared by adding TMP.I to a mixture of 70% egg PC and 100% egg PC/Chol (1:1 molar ratio), and used for the anti-metastasis experiment. B16F10 melanoma cells of $2\times10^5$ concentration were injected through tail veins of C57BL mice. Mice were treated with 250 µg of TMP.I-containing liposomes 1 hr after the injection of melanoma cell, treated with 250 µg of TMP.I-containing liposomes 3 days after the second injection of melanoma cell, and also treated with 250 µg of TMP.I-containing liposomes 7 days after the third injection of melanoma cell. Lungs were obtained from each group after 15 days of the first injection of melanoma cells by removal after killing them by dislocating the cervical vertebra and colony numbers were compared (Table 2).

TABLE 2

Result of Anti-metastatic Activity of TMP-I Liposomes comprising 70% PC and 100% PC

| Classification | Dose of TMP-I (µg) | No. of Colonies |
|---|---|---|
| PBS | — | 200 ± 20 |
| 70% PC/TMP-I Liposome (10:1 wt ratio) | 250 | 35 ± 15 |
| 100% PC/Chol/TMP-I Liposome (5:5:1 mole ratio) | 250 | 30 ± 10 |

Experimental Example 3

The anti-metastatic activity of TMP.I concentration was examined using liposome compositions comprising 70% egg PC. Liposomes were added with cholesterol in addition to 70% egg PC in order to increase the stability of liposomes. The experiments of anti-metastatic activity were carried out with liposomes containing mixture of 70% egg PC, Chol, and TMP.I.

The result showed that liposomes containing 50 µg of TMP I had more than 60% of anti-metastatic activity (FIG. 1 and Table 3). In contrast, the conventional TMS.hal (trimethylsphingosinium halide) liposomes with 250 µg TMS showed about 50% of anti-metastatic activity (Y. S. Park et al., Cancer Res., 54, 2213–2217, 1994). Thus, it turned out that the anti-metastatic effect of TMP.I liposomes was superior to that of TMS liposomes.

TABLE 3

Anti-metastatic Activity according to different TMP-I Contents

| Classification | Dose of TMP-I (µg) | No. of Colonies |
|---|---|---|
| PBS | — | >250 |
| 70% PC/Chol/TMP-I liposome | 50 | 80 ± 30 |

TABLE 3-continued

Anti-metastatic Activity according to different TMP-I Contents

| Classification | Dose of TMP-I (μg) | No. of Colonies |
| --- | --- | --- |
| (4:4:1 wt ratio) | 100 | 30 ± 10 |
|  | 200 | 35 ± 25 |

Experimental Example 4

Anti-metastatic activities of various anti-metastatic liposomes were examined according to different compositions and also the liposomes added with anti-angiogenic agent (AG3340, Agouron Pharmaceuticals, USA) were examined for the anti-metastatic activities (Table 4). Control liposomes were prepared by mixing 70% egg PC/Chol/Phytosphingosine in 4:4:1 wt ratio. Lipid to drug ratio was kept to 20:1 wt ratio. The liposome compositions and the effects are shown in the following table 4. The concentrations of TMP.I and drugs (anti-angiogenic drugs) being administered were both set at 100 μg, and the TMP.I concentration remained the same regardless of the presence of a drug (an anti-angiogenic drug) in a given liposome.

Figure 2:
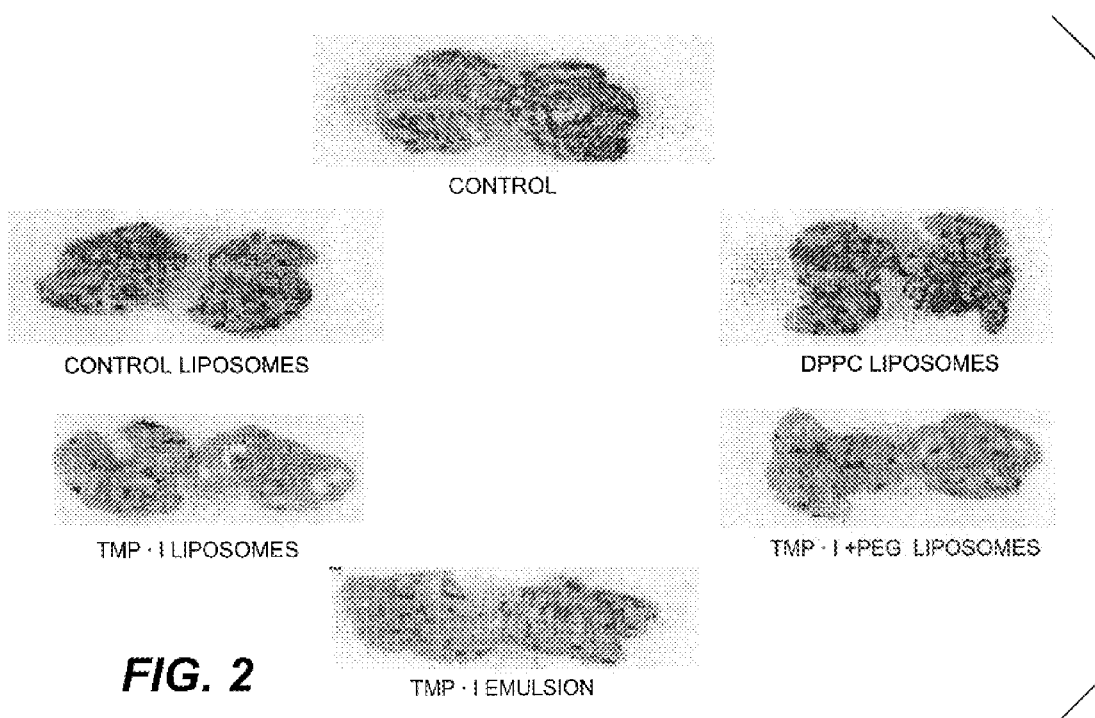
FIG. 2 shows pictures representing the anti-metastatic activity of TMP.I liposomes and TMP.I emulsion, wherein both of which contain an anti-angiogenic compound.

Experiments were carried out the same as in Example 5 with the exception that administrations of liposomes were performed four times of 1 hr, 3 days, 6 days and 9 days after the injection of melaionia cells. The result showed that the number of colonies slightly decreased in control group of liposomes comprising phytosphingosine, however, the effect was not noticeable. When the administration was performed by DPPC liposomes along with a drug (an anti-angiogenic drug) there was almost little anti-metastatic effect shown. However, when the administration was performed by TMP.I-containing liposomes along with a drug (an anti-angiogenic drug), the colony numbers were remarkably reduced to less than fifteen in count. When (TMP.I+PEG) liposomes, liposomes wherein 10% PEG-PE is added to TMP.I-containing liposomes, were administered to increase the retention time of liposomes in blood, similar superior effect was observed (FIG. 2).

TABLE 4

Examination of Synergistic Anti-metastatic Activity of TMP-I-containing Liposomes with the Addition of Anti-angiogenic agent

| Classification | Dose of TMP-I (μg) | Anti-angiogenic Agent (μg) | No. of Colonies |
| --- | --- | --- | --- |
| PBS | — | — | >250 |
| Control Liposomes[1] | — | — | 200 ± 30 |
| DPPC Liposomes[2] | — | 100 | 210 ± 40 |
| TMP-I Liposomes[3] | 100 | 100 | 15 ± 5 |
| TMP-I Liposomes[3] | 100 | — | 35 ± 10 |
| TMP-I + PEG Liposomes[4] | 100 | 100 | 15 ± 5 |

[1]70% PC/Chol/Phytosphingosine (4:4:1 wt ratio)
[2]DPPC/Chol (1:1 mole ratio)
[3]DPPC/Chol/TMP-I (5:5:1 mole ratio)
[4]DPPC/Chol/PEG-PE/TMP-I (5:5:1:1 mole ratio)

Experimental Example 5

Anti-metastatic activity was measured by using an emulsion prepared from a TMP.I derivative having anti-metastatic activity. Experiments were carried out as in Experimental Example 4 with the exception that the anti-metastatic emulsion was intraperitoneally administered. The lungs obtained from an untreated group (a control group) were compared with those treated with a TMP.I emulsion. The results showed that there were 250 colonies in the control group while there were 70±20 colonies in the group treated with a TMP.I emulsion. This value implies that anti-metastatic activity was more than 70% (FIG. 2).

Experimental Example 6

TMP.I liposomes (DPPC/Chol/TMP.I=5:5:1 mole ratio) having an anti-metastatic activity, was administered to BDF1 inoculated with Lewis Lung Carcinoma (LLC) cells and their inhibitory effect on the tumor growth was observed. The concentration of LLC cancer cells used was one million cancer cells per each mouse and tumor was induced by subcutaneous injection. One day after the subcutaneous injection, TMP.I liposomes were introduced into each mouse via intravenous injection and intraperitoneal injection (TMP.I content: 100 μg). The same administration was repeated after 3 days, 6 days and 9 days of the subcutaneous injection of the LLC cancer cells and 21 days after the injection each mouse was killed by dislocation of the cervical vertebra, and the volume of cancer was measured by the following equation and the results are shown in the following table 5.

$$(\text{Long Axis of Cancer}) \times (\text{Short Axis of Cancer})^2 / 2 \quad [\text{Equation 1}]$$

TABLE 5

Administration Routes and Number of Dose for TMP-I Liposomes and AG3340 (a positive control) and the results on the Inhibition of Cancer Growth

| Classification | Amount of Dosage (μg) | Adm. Routes./ Number of Dose | Volume of Cancer (mm³) | Inhibition Rate (%) |
| --- | --- | --- | --- | --- |
| Control |  |  | 1587 ± 400 | 0 |
| AG3340 | 2000 | intraperitoneal/20 | 1100 ± 250 | 31 |
| TMP-I | 100 | intraperitoneal/4 | 220 ± 50 | 87 |
| TMP-I | 100 | intravenous/4 | 540 ± 150 | 66 |

As shown in the above, the volume of cancer grew very large in a control group and it showed that there was an active angiogenic progress around the cancer region. In the group where TMP.I liposomes were intraperitoneally injected, the volume of cancer was remarkably decreased and the angiogenic progress was also much deteriorated. Meanwhile, in the group where 2000 μg of AG3340, an MMP-2 inhibitor, was injected daily for the duration of 20 days after suspending it in tween/carboxymethyl cellulose, the volume of cancer was not much reduced; i.e., when AG3340, a positive control, was intraperitoneally injected there was a decrease of only about 30% in the volume of cancer. In contrast, when TMP liposomes were abdominally injected there was a decrease in volume of about 85% while there was about 60% decrease in cancer volume when TMP liposomes were injected intravenously.

Experimental Example 7

Figure 3:
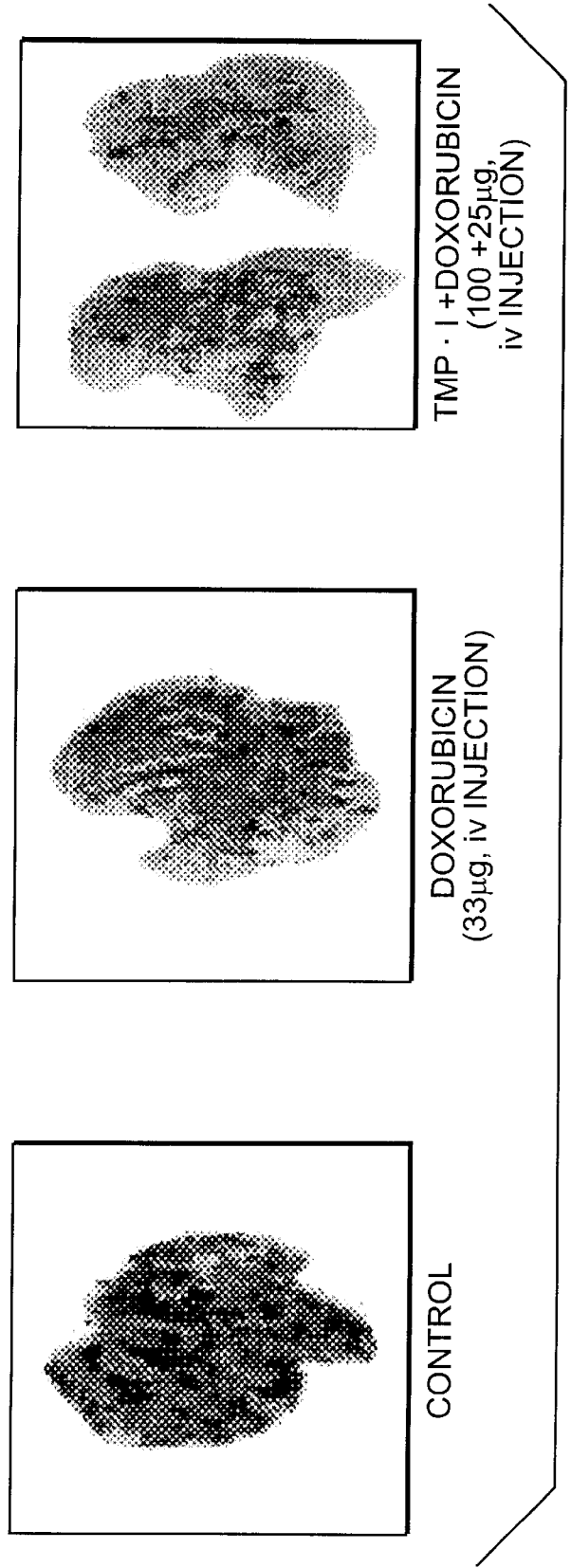
FIG. 3 shows pictures representing the relationship between TMP.I liposomes and doxorubicin, an antitumor agent.

The effects of TMP.I liposomes and doxorubicin, the conventional anititumor agent with cytotoxic agent, on metastasis in mice were examined by using B16F10 melanoma cells. The melanoma cells of 2×10⁵ per each mouse were intravenously injected, 33 μg of doxorubicin were administered immediately after the injection and also 3 days, 6 days and 9 days after tile intravenous injection, respectively, and in another group was administered with 25 μg of doxorubicin along with TMP.I liposomes. The result showed that anti-metastasis was more effective when TMP.I liposomes were administered in addition to doxorubicin than when doxorubicin was administered alone, even when less amount of doxorubicin was used (FIG. 3).

Experimental Example 8

Figure 4:
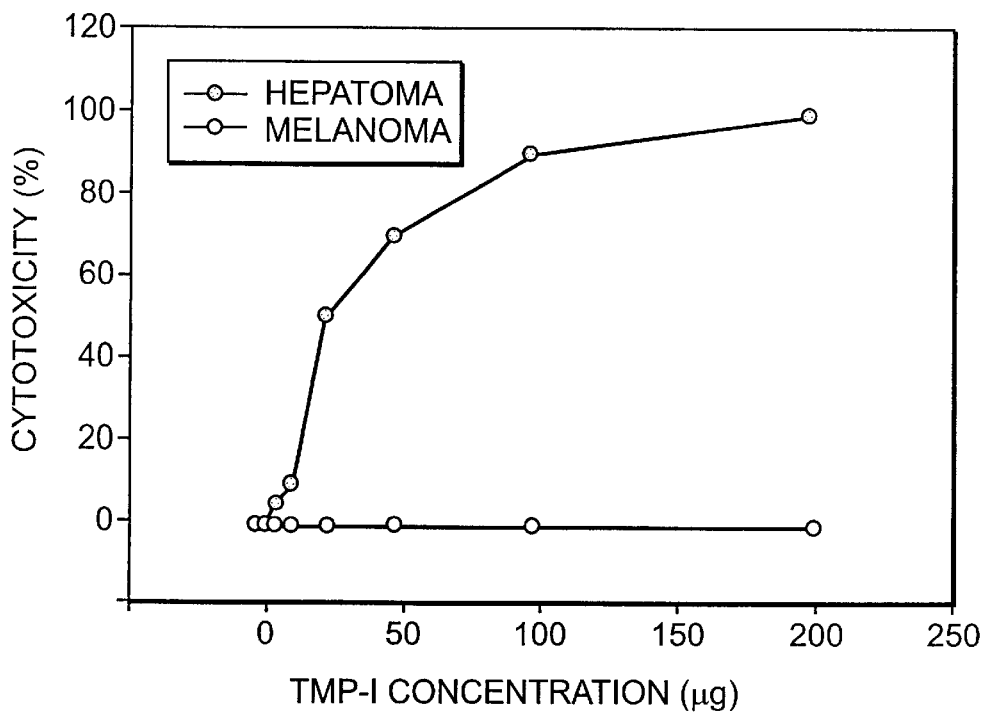
FIG. 4 is a graph showing the cytotoxicity of a cationic liposome that contains TMP.I.

Two different kinds of TMP.I liposomes were manufactured to examine in vivo toxicity and the cytotoxicity. The two TMP.I-containing cationic liposomes, DOPE/TMP and DPPC/Chol/TMP liposomes, were used to examine their cytotoxic effects on cancer cells. The hepatoma cell lines used were Human hepatoma cell line SNU398 and mouse melanoma cell line B16F10. The cationic liposomes (TMP.I:DOPE=1:1 wt ratio) were prepared in various concentrations and their cytotoxic effects on cancer cells were examined accordingly (FIG. 4). The result showed that there was no cytotoxic effect observed in mouse melanoma cell line (up to 200 µg) while there was observed some death of cancer cells in human hepatoma cells when these hepatoma cell lines were treated with 12.5 µg of TMP.I liposomes and almost all cancer cells were dead when treated with 100 µg of TMP.I liposomes. In case of SNU cancer cells, $LD_{50}$ was 25 µg (FIG. 4).

When mice were intraperitoneally injected with 2000 µg of TMP.I-containing cationic liposomes and the same injection was repeated 3 days and 6 days after the first injection, respectively, and examined 15 days after the first injection, the mice were observed still alive. Moreover, when mice were intravenously injected with 1000 µg of DPPC/Chol/TMP.I liposomes 3 times as in the above and examined 15 days after the first injection, they were also still alive (Table 6).]

TABLE 6

In vivo Toxicity Test of TMP-I-containing Liposomes

| Classification | Amount of Dosage (µg) | Adm. Routes | Number of Dosage | Lethality Rate (%) |
|---|---|---|---|---|
| DOPE/TMP-I | 2000 | intraperitoneal | 3 | 0/5 (0) |
| DPPC/Chol/TMP-I | 1000 | intravenous | 3 | 0/5 (0) |

Experimental Example 9

Figure 5:
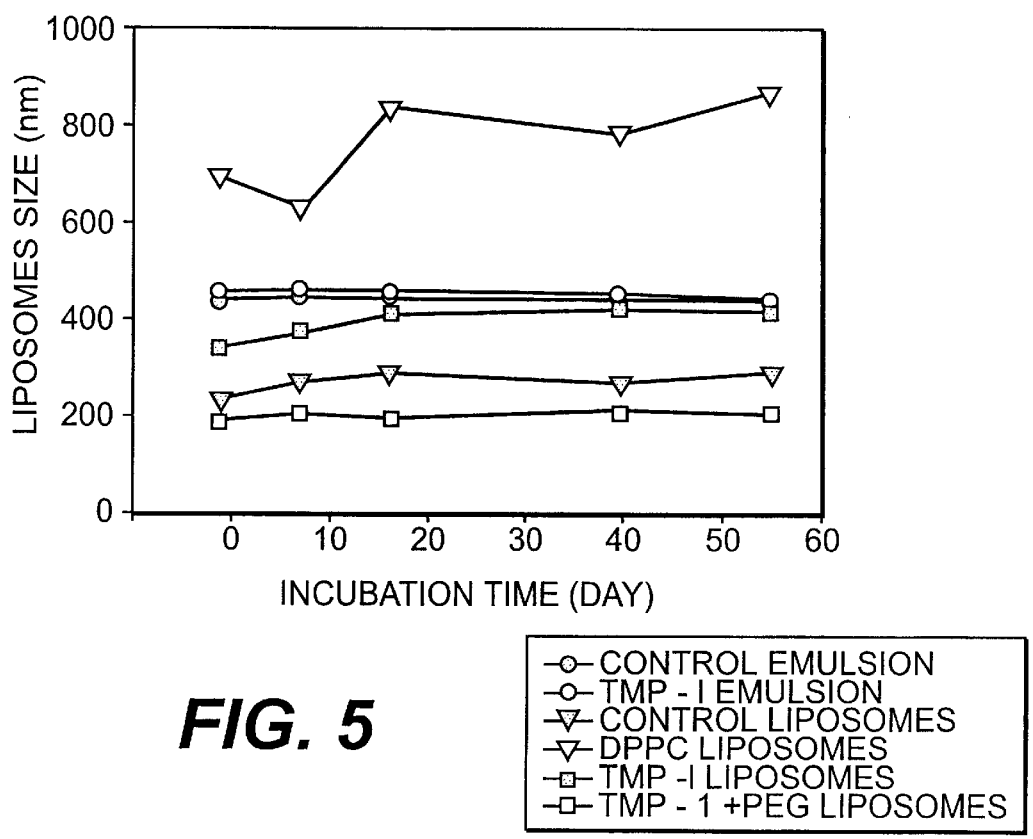
FIG. 5 is a graph showing the stability of various liposomes and emulsions containing a TMP derivative stored at 4° C.

The stability of anti-metastatic liposomes and anti-metastatic emulsions kept at 4° C. were examined by using zetasizer 3000 according to the change in size of liposomes and emulsions. The result showed that cationic TMP.I liposomes were stable in distilled water and a 5% dextrose solution. In case of PC-based liposomes, liposomes that contain DPPC and PEG-PE were most stable and the emulsions were also shown stable for the period of two months (FIG. 5).

As shown in the above, the present invention provided multi-functional liposomes comprising TMP, a phytosphingosine derivative of formula I, which can not only inhibit the metastasis and growth of cancer cells but also optimize the anti-metastatic effect when used in combination of other kinds of antitumor agents. Unlike conventional liposomes, these anit-metastatic liposomes can exhibit anti-metastatic activities alone and thus they will be very useful in the delivery system of an antitumor agent and also able to reduce the amount of the dosage level of a given antitumor agent.

What is claimed is:

1. An antitumor agent comprising (a) a substance of anti-angiogenic activity or a cytotoxic cancer drug and (b) a phytosphingosine derivative of formula I as an active ingredient,

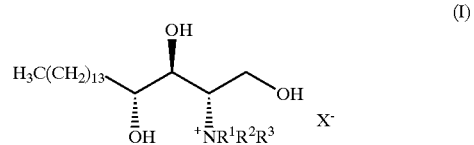

(I)

wherein $R^1$, $R^2$ and $R^3$ respectively represents a hydrogen atom or a $C_1$–$C_8$ alkyl group with the proviso that $R^1$, $R^2$, and $R^3$ do not simultaneously represent a hydrogen atom; and X represents an atom or atomic group containing a halogen atom, a hydroxyl group, an alkyl sulfonate group or an aryl sulfonate group; and wherein said phytosphingosine derivative is contained in a form of a liposome or am emulsion.

2. An antitumor agent of claim 1, wherein said phytosphingosine derivative is a N,N,N-trimethylphytosphingosinium halide.

3. A method of making an antitumor agent, comprising including, in said antitumor agent, (a) a substance of anti-angiogenic activity or a cytotoxic cancer drug and (b) a phytosphingosine derivative of formula I as an active ingredient,

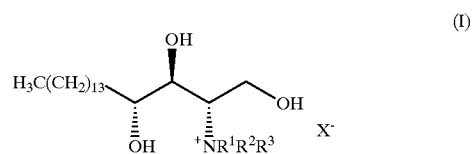

(I)

wherein $R^1$, $R^2$ and $R^3$ respectively represents a hydrogen atom or a $C_1$–$C_8$ alkyl group with the proviso that $R^1$, $R^2$, and $R^3$ do not simultaneously represent a hydrogen atom; and X represents an atom or atomic group containing a halogen atom, a hydroxyl group, an alkyl sulfonate group or an aryl sulfonate group; and wherein said phytosphingosine derivative is contained in a form of a liposome or an emulsion.

4. A method of claim 3, wherein said phytosphingosine derivative is a N,N,N-trimethylphytosphingosinium halide.

5. A method of inhibiting cancer cell growth in a human or a mouse in need thereof, comprising administering to said human or said mouse in need of inhibiting cancer cell growth a phytosphingosine derivative of formula I as an active ingredient,

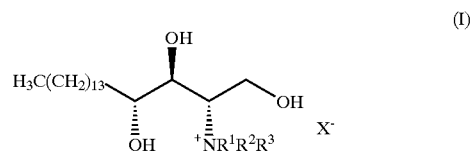

(I)

wherein $R^1$, $R^2$ and $R^3$ respectively represents a hydrogen atom or a $C_1$–$C_8$ alkyl group with the proviso that $R^1$, $R^2$, and $R^3$ do not simultaneously represent a hydrogen atom; and X represents an atom or atomic group containing a halogen atom, a hydroxyl group, an alkyl sulfonate group or an aryl sulfonate group.

6. A method of claim 5, wherein said phytosphingosine derivative is a N,N,N-trimethylphytosphingosinium halide.

7. A method of claim 5, wherein said phytosphingosine derivative is contained in a form of a liposome or an emulsion.

8. A method of claim 5, further comprising administering to said human or said mouse a substance of anti-angiogenic activity or a cytotoxic cancer drug.

9. A method of claim 7, further comprising administering to said human or said mouse a substance of anti-angiogenic activity or a cytotoxic cancer drug.

10. A method of claim 9, wherein said phytosphingosine derivative is contained in a form of a liposome or an emulsion.

* * * * *